United States Patent
Pfaffernoschke et al.

(10) Patent No.: US 7,341,714 B2
(45) Date of Patent: Mar. 11, 2008

(54) PEARLESCENT HAIR CARE COMPOSITIONS

(75) Inventors: Matthias Pfaffernoschke, Aaberg (CH); Sybille Jungo, St. Ursen (CH)

(73) Assignee: Wella AG, Darmstadt (DE)

( * ) Notice: Subject to any disclaimer, the term of this patent is extended or adjusted under 35 U.S.C. 154(b) by 452 days.

(21) Appl. No.: 10/253,291

(22) Filed: Sep. 24, 2002

(65) Prior Publication Data

US 2003/0068292 A1 Apr. 10, 2003

(30) Foreign Application Priority Data

Sep. 26, 2001 (DE) ............... 101 47 501

(51) Int. Cl.
*A61Q 5/12* (2006.01)
(52) U.S. Cl. ............... 424/70.11; 424/70.15; 424/70.19; 424/70.21; 424/70.27
(58) Field of Classification Search ............ None
See application file for complete search history.

(56) References Cited

U.S. PATENT DOCUMENTS 6,210,659 B1 * 4/2001 Wilhelm et al. ......... 424/70.24
6,528,046 B1 * 3/2003 Schmenger et al. ....... 424/70.1

FOREIGN PATENT DOCUMENTS

| EP | 0 376 083 A2 | 7/1990 |
| WO | 96/40815 | 12/1996 |
| WO | 01/28505 A1 | 4/2001 |

OTHER PUBLICATIONS

Schrader: "Grundlagen und Rezepturen Der Kosmetika", 2. Auflage, 1989, pp. 728-737 (with Statement of Relevancy and English Translation).
Pheological Properties of Cosmetics and Toiletries, Rheology of Hair Products, Edited by Dennis Laba, pp. 307-308 (Admitted Prior Art).
Fomulators Forum, Cosmetics & Toiletries Magazine, vol. 116, No. 12/Dec. 2001, pp. 30, 32, 34.
Dispersionen Und Emulsionen, Darmstadt: Steinkopff, 1997, pp. 466-469. (With English Translation).

* cited by examiner

*Primary Examiner*—Jyothsna Venkat
(74) *Attorney, Agent, or Firm*—Michael J. Striker

(57) ABSTRACT

The hair treatment composition, which is in the form a pearlescent product, contains a nonionic, amphiphilic associative thickener consisting of at least one hydrophobically modified aminoplast/polyether copolymer; a hair care active ingredient selected from the group consisting of cationic surfactants, zwitterionic surfactants, cationic polymers, cationic silicone compounds, amine-substituted silicone compounds, cationic derivatized proteins, cationic derivatized protein hydrolyzates and betaines; and a pearlescence or turbidity-inducing agent selected from the group consisting of fatty acid alkanol amides, fatty acid glyceryl esters, guanine, glycol fatty acid diesters, styrene/acrylate copolymers, polyethylene glycol fatty acid diesters, styrene/vinyl pyrrolidone copolymers and poly(trimethylammonium ethylmethacrylate chloride); in an aqueous cosmetic base. The composition is usable as a leave-in hair care composition or a hair rinse, which conditions the hair and imparts luster and volume to the hair.

20 Claims, No Drawings

PEARLESCENT HAIR CARE COMPOSITIONS

BACKGROUND OF THE INVENTION

The subject matter of the present invention is a hair treatment composition, which is useable as a hair rinse or especially as a leave-in hair care composition, which is in the form of a pearlescent product and which contains a certain associative thickener, cationic hair care ingredients and certain pearlescence or turbidity-inducing agents.

Conventional hair conditioning preparations, such as rinse-off care compositions or leave-on hair treatment agents, are usually formulated on the basis of aqueous emulsions. Cation-active substances, especially fatty alcohol, emulsifiers, and additional specific active and perfume materials, are essential ingredients. The most important ingredients are cationic surfactants, fatty alcohol and emulsifiers. The preparations appear milk white and can contain pearlescence agents in order to improve the pearlescence effect. A review of the principal composition of care rinses and hair care compositions is given by Schrader, in "Grundlagen und Rezepturen der Kosmetika{Foundations and Formulations of Cosmetics}", 2nd Edition, 1989, pp. 728 to 737. The principal purposes of conditioning agents are the improvement of the stylability, the combability, the luster and the feel of the treated hair.

The known emulsion-form hair care compositions based on cationic surfactants and fatty alcohol have production engineering problems. The solid fatty alcohol usually must be melted and emulsified at elevated temperatures. The manufacturing and cooling processes have a considerable influence on the product quality, especially the product consistency and the quality of the pearlescence effect. The pearlescence effect strongly depends on the course of the temperature during cooling. In the cooling phase the product passes through a visco-elastic state and problems due to crystallizing out can occur at elevated temperatures. However the course of the temperature during cooling is frequently unpredictable and very difficult to reproduce in a controlled manner. The result is that there are considerable fluctuations in the emulsion stability, viscosity and pearlescence effect during production and many production runs are not satisfactory. Subsequent thickening is usually not possible.

SUMMARY OF THE INVENTION

It is the purpose of the present invention to provide a hair-conditioning hair care composition, which has a beautiful pearlescence effect, at least equally satisfactory hair conditioning properties as a conventional hair care composition based on an aqueous emulsion of cationic surfactants and fatty alcohol and at the same time has improved stability in regard to pearlescence and viscosity, and which is easily produced with reliable quality.

Hair treatment compositions having the following described compositions attain this purpose or object. According to the invention the pearlescent hair care composition comprises an aqueous cosmetic base and a combination of (A) at least one nonionic, amphiphilic associative thickener consisting of at least one hydrophobically modified aminoplast/polyether copolymer;

(B) at least one hair care active ingredient selected from the group consisting of cationic surfactants, zwitterionic surfactants, cationic polymers, cationic silicone compounds, amine-substituted silicone compounds, cationic derivatized proteins, cationic derivatized protein hydrolyzates and betaines; and (C) at least one pearlescence or turbidity-inducing agent selected from the group consisting of fatty acid alkanol amides, fatty acid glyceryl esters, guanine, glycol fatty acid diesters, styrene/acrylate copolymers, polyethylene glycol fatty acid diesters, styrene/vinyl pyrrolidone copolymers and poly(trimethylammonium ethylmethacrylate chloride);

in the aqueous cosmetic base.

The nonionic, amphiphilic associative thickener (A) is contained in the compositions of the invention in an amount of preferably 0.1 to 5 percent by weight, especially preferably of 0.1 to 2 percent by weight. The hair care active ingredient (B) is preferably contained in an amount of preferably in an amount of 0.01 to 10, especially preferably from 0.1 to 5, percent by weight. The pearlescence or turbidity-inducing agent (C) is contained in the compositions of the invention preferably in an amount of 0.1 to 10 percent by weight, especially preferably of 0.5 to 6 percent by weight. The composition is preferably substantially free of fatty alcohol, i.e. it contains no or less than 0.2 percent by weight of fatty alcohol.

These compositions according to the invention fulfill the specifications for a hair conditioning composition regarding conditioning action in the best possible way, have a very good pearlescence effect and are characterized by a reliable manufacturing process and improved product stability. Also the compositions according to invention are stable regarding their product consistency and pearlescence during long term storage. Hair treated with the compositions according to the invention is notably smoother in both the moist and dry state. The wet combability is noticeably improved. Surprisingly these effects are attained without the unavoidable fatty alcohol in commercial hair care compositions. Because of the beautiful pearlescence effect that has long-term stability, it is possible to fill the composition according to the invention in an optically pleasing translucent or transparent package. The composition according to the invention can be packaged, for example in glass or transparent plastic, such as a polyethylene, polypropylene or polyethylene terephthalate.

The nonionic amphiphilic associative thickener (A) is a polymer, which contains both hydrophilic and hydrophobic groups. Associative thickeners are water-soluble polymers and have surfactant-like hydrophobic parts, which are in a position to associate both with themselves and also with other hydrophobic materials in a hydrophilic, especially aqueous, medium. The medium is thickened or gels because of the resulting associative network. Typically associative thickeners are made by polymerization of polyethylene oxide pre-polymers and polycondensible materials with at least two functional groups, such as isocyanates. Monohydroxy compounds or dihydroxy compounds are built in with large aryl groups, alkyl groups or aryl/alkyl groups, in order to prepare the hydrophobic modifications. Hydrophobically modified polyalkylene glycols are preferred associative thickeners. The hydrophilic functional groups are preferably formed by polyoxyalkylene units, preferably polyoxyethylene, but also polyoxypropylene units or their mixtures. The hydrophobic parts are preferably formed by hydrocarbon groups, especially long-chain alkyl groups, alkyl aryl groups or arylalkyl groups. A suitable associative thickener is a reaction product of an acid catalyzed reaction of a glycoluril derivative compound, a polyalkylene glycol and an alkoxylated hydrocarbon.

The associated thickeners are hydrophobically modified aminoplast polyether copolymers. WO 96/40815 describes the structure and manufacture of these latter compounds. Water-dispersible or water-soluble copolymers are described in WO 96/40815, which are the acid catalyzed reaction products of aminoplast monomers with at least two functional groups and alkylene polyethers with at least two functional groups as well as functional compounds with hydrophobic groups. Suitable aminoplasts are shown in FIG. 1 of WO 96/40815. The glycoluril derivatives of formula X of WO 96/40815 are especially preferred. Suitable alkylpolyethers are shown in FIG. 2 of WO 96/40815. Preferred alkylene polymers are polyethylene oxide diols. These compounds can have an ethoxylation degree of 20 to 500, preferably 50 to 350 and especially preferably from 100 to 250. The compounds of formula XIV of WO 96/40815 are suitable simple compounds with hydrophobic groups. According to the invention suitable associative thickeners are preferably selected from the group consisting of polymers of the general formula (I):

(I)

wherein Amp represents an aminoplast monomer or an aminoplast oligomer group or an aminoplast polymer group; AO represents an alkylene oxide group, R represents hydrogen, a $C_1$- to $C_4$-alkyl group or a $C_1$- to $C_4$-acyl group, x and y are greater than 1 and n is a positive number.

The reaction products of acid catalyzed polycondensation of (a) glycolurils of the general formula (II) are especially preferred as the associative thickener,

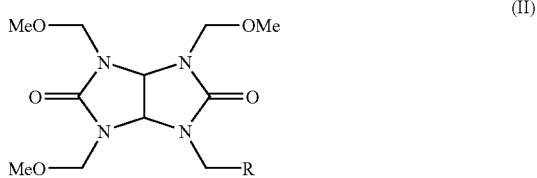

(II)

wherein R represents H or preferably OMe, with (b) polyethylene oxide diols having an ethoxylation degree of 20 to 500, preferably 50 to 350, especially preferably from 100 to 250, and, if necessary, with (c) an ethoxylated hydrophobic alcohol, alkyphenol, thiol, carboxamide, carbamate or a hydrophobic carboxylic acid, as described on pages 17 to 19 of WO 96/40815.

1,3,4,6-tetramethoxymethyl glycoluril (TMMG) is especially preferred as the glycouril used in the hair care or hair treatment compositions of the invention.

Suitable associative thickeners are those with the following INCI names: polyether-1, PEG-180/octoxynol-40/TMMG copolymer and PEG-180/Laureth-50/TMMG copolymer. These compounds are, for example, marketed by Süd-Chemie A G, München, Germany, under the trademark Pure-Thix® HH, L and M.

The hair care ingredient (B) is a substance, which has a substantive action on human hair because of its cationic or cationizable groups, especially primary, secondary, tertiary or quaternary amine groups. Suitable cation-active substances are selected from the group consisting of cationic surfactants, zwitterionic, especially betainic surfactants, cationic silicone compounds, amine-substituted silicone compounds, cationic organic polymers with cationic or cationizable groups, cationic derivatized proteins, cationic protein hydrolyzates and betaine.

Suitable cationic surfactants are surfactants, which contain quaternary ammonium groups. Preferred cationic surfactants are represented by the general formula III:

(III)

wherein $R^1$ to $R^4$ each represent, independently of each other, an aliphatic group, an aromatic group, an alkoxy group, a polyoxyalkylene group, an alkylamido group, a hydroxyalkyl group, an aryl group or an alkaryl group, each with 1 to 22 carbon atoms, and $X^{(-)}$ represents an anion, especially halogen, acetate, phosphate, nitrate or alkylsulfate, preferably chloride. The aliphatic groups can also have cross-linkages or other groups in addition to hydrogen and carbon, such as hydroxy or amino groups. At least one of the substituents $R^1$ to $R^4$ is an alkyl or alkenyl group with one or more double bonds, which has at least eight carbon atoms. Fattyalkyltrimethyl ammonium and difattyalkyldimethylammonium compounds are especially preferred. For example, the following are suitable cationic surfactants: the chlorides or bromides of alkyldimethylbenzyl ammonium salts, alkyltrimethyl ammonium salts, especially cetyltrimethyl ammonium chloride or cetyltrimethyl ammonium bromide, tetradecyltrimethyl ammonium chloride or tetradecyltrimethyl ammonium bromide, alkyldimethylhydroxyethyl ammonium chloride or alkyldimethylhydroxyethyl bromide, dialkyldimethyl ammonium chloride or dialkyldimethyl ammonium bromide, alkylpyridinium salts, especially laurylpyridinium chloride or cetylpyridinium chloride, alkylamidoethyl trimethyl ammonium ether sulfate and compounds with cationic character, such as amine oxides, especially alkylmethylamine oxide or alkylaminoethyldimethylamino oxide. Cetyltrimethyl ammonium chloride, behenyltrimethylammonium chloride and stearyltrimethylammonium chloride are particularly preferred.

Suitable zwitterionic surfactants are derivatives of aliphatic quaternary ammonium, phosphonium and sulfonium compounds of formula (IV):

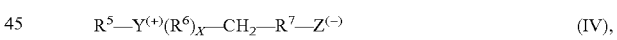

(IV), wherein $R^5$ is a straight chain or branched alkyl-, alkenyl- or a hydroxyalkyl group with 8 to 18 carbon atoms and from 0 to about 10 ethylene oxide units and 0 to 1 glyceryl unit; Y represents an N-, P- or S-containing group; $R^6$ represents an alkyl or monohydroxyalkyl group with one to three carbon atoms; X is equal to one in case that Y is a sulfur atom and X is equal to 2 in case Y is a nitrogen or a phosphorous atom; $R^7$ is an alkylene or hydroxy-alkylene group with one to four carbon atoms and $Z^{(-)}$ represents a carboxylate, sulfate, phosphonate or phosphate group. Other amphoteric surfactants, such as betaines, are similarly suitable for the compositions according to the invention. These betaines include, for example, $C_8$- to $C_{18}$-alkylbetaines, such as cocodimethylcarboxymethylbetaine, lauryldimethylcarboxymethylbetaine, lauryldimethylalphacarboxyethylbetaine, cetyldimethylcarboxymethylbetaine, oleyldimethylgammacarboxypropylbetaine and lauryl-bis-(2-hydroxypropyl)alphacarboxyethylbetaine; $C_8$- to $C_{18}$-sulfo-betaines, such as cocodimethylsulfopropylbetaine, cetearyl-dimethyl-sulfopropyl-betaine, lauryldimethylsulfoethylbetaine, lauryl-bis-(2-hydroxyethyl)sulfo-propylbetaine; carboxyl derivatives of imidazoles, $C_8$- to $C_{18}$-alkyldimethyl ammonium acetate, $C_8$- to $C_{18}$-alkyldimethylcarbonylmethyl ammonium salts and $C_8$- to $C_{18}$-fatty acid alkylamido betaines, such as coconut oil fatty acid amidopropylbetaine, which is marketed in the form of a 30 % aqueous solution under the trademark TEGO® Betaine L7 of Goldschmidt AG and N-coconut oil fatty acid amidoethyl-N-[2-(carboxymethoxy)ethyl]-glycerol (CFTA name: cocoamphocarboxyglicinate), which is marketed, for example, in the form of a 50% aqueous solution under the trademark MIRANOL® C2M of Miranol Chemical Co. Inc. Coconut fatty acid amidopropylbetaine is particularly preferred.

The suitable cation-active polymers are preferably hair-fixing or hair-conditioning polymers. Suitable polymers of ingredient (C) contain preferably quaternary amine groups. The cationic polymers can be homopolymers or copolymers, in which the quaternary nitrogen groups either are contained in polymer chains or backbones or preferably as substituents in one or more of the monomers. Monomers containing ammonium groups monomers can be copolymerized with non-cationic monomers. Suitable cationic monomers include unsaturated, radically polymerizable compounds, which have at least one cationic group, especially ammonium-substituted vinyl monomers, such as trialkylmethacryloxyalkyl ammonium groups, trialkylacryloxyalkyl ammonium groups, dialkyldiallyl ammonium groups and quaternary vinyl ammonium monomers with cyclic, cationic nitrogen-containing groups, such as pyridinium, imidazolium or quaternary pyrrolidone groups, e.g. alkylvinyl imidazolium, alkylvinylpyridinium, or alkylvinylpyrrolidone salts. The alkyl groups of these monomers are preferably lower alkyl groups, preferably $C_1$- to $C_7$-alkyl groups, especially preferably $C_1$- to $C_3$-alkyl groups.

The monomers containing the ammonium groups can be copolymerized with non-cationic monomers. Suitable comonomers are, for example, acrylamide, methacrylamide, alkylacrylamides, dialkylacrylamides, alkylmethacrylamides, dialkylmethacrylamides, alkylacrylates, alkylmethacrylates, vinyl caprolactone, vinylcaprolactam, vinyl pyrrolidone, vinyl esters, e.g. vinyl acetate, vinyl alcohols, propylene glycol or ethylene glycol. The alkyl groups of these monomers are preferably $C_1$- to $C_7$-alkyl groups, especially preferably $C_1$- to $C_3$-alkyl groups.

Suitable cationic polymers with quaternary amino groups are, for example, the polymers described in the CTFA Cosmetic Ingredient Dictionary under the trade name, polyquaternium, for example methylvinylimidazolium chloride/vinyl pyrrolidone copolymer (polyquaternium-16) or quaternized vinyl pyrrolidone/dimethylaminoethyl-methacrylate copolymer (polyquaternium-11). Especially preferred examples of the cationic polymers, which can be contained in the compositions of the invention, include for example, vinylpyrrolidone/dimethylaminoethylmethacrylate methosulfate copolymer. This latter copolymer is sold under the trademarks GAFQUAT® 755N and GAFQUAT® 734 of GAF Co., USA, is especially suitable as the cationic polymer in the compositions according to the invention. GAFQUAT® 734 of GAF Co., USA, is especially preferred. Additional suitable cationic polymers, are, for example, the copolymer of polyvinyl pyrrolidone and imidazolimine methochloride, marketed under the trademark LUVIQUAT® HM 550 of BASF, Germany; the terpolymer of dimethyidiallyl ammonium chloride, sodium acrylate and acrylamide sold under the trademark MERQUAT® Plus 3300 by Calgon, USA; the terpolymer of vinyl pyrrolidone, dimethylaminoethylmethacrylate and vinyl caprolactam marketed under the trademark GAFFIX® VC 713 of ISP, USA; and vinyl pyrrolidone/methacrylamidopropyltrimethyl ammonium chloride copolymer marketed under the trademark GAFQUAT® HS 100 of GAF Inc.

Suitable cationic polymers, which are derived from natural polymers, include cationic derivatives of cellulose, starch or guar. Chitosan and chitosan derivative compounds are suitable. Suitable polysaccharides have the general formula (V):

$$G-(O-B-N^+R^aR^bR^c)_n X^{(-)} \qquad (V),$$

wherein G is a anhydroglucose residue, for example starch or cellulose anhydroglucose and n is a number greater than 0; B is a divalent group, for example, an alkylene, an oxyalkylene, a polyoxyalkylene or hydroxyalkylene; $R^a$, $R^b$ and $R^c$ are each, independently of each other, alkyl, aryl, alkylaryl, arylalkyl, alkoxyalkyl or alkoxyaryl with up to 18 carbon atoms respectively, wherein the total number of carbon atoms in $R^a$, $R^b$ and $R^c$ is at most 20; X is a common counter anion and is the same as in formula (III) and is preferably chloride. A cationic cellulose compound is marketed under the trade name Polymer JR of Amerchol and has the INCI name, polyquaternium-10. An additional cationic cellulose compound has the INCI name, polyquaternium-24, and is marketed by Amerchol under the trade name, Polymer LM-200, A suitable cationic guar derivative compound is marketed under the trade name Jaguar R and has the INCI name, guar hydroxypropyltrimonium chloride.

Neutralized chitosans and chitosan derivative compounds are especially preferred as the cationic materials. The chitosan used in the compositions of the invention is partially or completely deacetylated. The molecular weights of chitosans can vary over a wide range, for example from 20,000 to 5,000,000 g/mol. A low molecular weight chitosan is, for example, considered to be a chitosan with a molecular weight of from 30,000 to 70,000 g/mol. For the purpose of the present invention the molecular weight preferably is above 100,000 g/mol, especially preferably from 200,000 to 700,000 g/mol. The deacetylation degree amounts to from 10 to 99%, especially preferably form 60 to 99%. A suitable chitosan is, for example, marketed under the trademark, FLONAC®, by Kyowa Oil & Fat, Japan. It has a molecular weight of 300,000 g/mol to 700,000 g/mol and is deacetylated from 70 to 80%. A preferred chitosan salt is chitosonium pyrrolidone carboxylate, which for example is marketed under the trade name Kytamer PC of Amerchol, USA. The chitosan obtained has a molecular weight of about 200,000 to 300,000 g/mol and is deacetylated up to 70 to 85%. Quaternary, alkylated or hydroxyalkylated derivative chitosan compounds, for example, the hydroxyethyl chitosan or hydroxybutyl chitosan, are suitable in the compositions according to the invention. The chitosans or chitosan derivative compounds should be present in neutralized or partially neutralized form when used in the compositions of the invention. The neutralization degree for the chitosan or the chitosan derivative compounds is preferably at least 50%, especially preferably between 70 and 100%, relative to the number of free base groups. In principle, all cosmetically compatible inorganic or organic acids may be used as neutralization agent, for example formic acid, tartaric acid, malic acid, lactic acid, citric acid, pyrrolidone carboxylic acid, hydrochloric acid, among others. Pyrrolidone carboxylic acid and lactic acid are especially preferred as the neutralization agent.

Further suitable cation-active hair-care compounds are cationically modified protein derivative compounds or cationically modified protein hydrolyzates and for example are known under the INCI name lauryldimonium hydroxylpropyl hydrolyzed wheat protein, lauryldimonium hydroxypropyl hydrolyzed caesin, lauryldimonium hydroxypropyl hydrolyzed collagen, lauryldimonium hydroxypropyl hydrolyzed keratin, lauryldimonium hydroxypropyl hydrolyzed silk, lauryldimonium hydroxypropyl hydrolyzed soy protein or hydroxypropyltrimonium hydrolyzed wheat, hydroxypropyltrimonium hydrolyzed caesin, hydroypropyltrimonium hydrolyzed collagen, hydroxypropyltrimonium hydrolyzed keratin, hydroxypropyltrimonium hydrolyzed rice bran protein, hydroxypropyltrimonium hydrolyzed silk, hydroxypropyltrimonium hydrolyzed soy protein, hydroxypropyltrimonium hydroxlyzed vegetable protein.

Suitable cationic derivatized protein hydrolyzates are mixed substances that can be obtained, for example, by reaction of alkaline, acidic or enzymatically hydrolyzed proteins with glycidyltrialkyl ammonium salts or 3-halo-2-hydroxypropyltrialkyl ammonium salts. Proteins, which act as starting materials for the protein hydrolyzates, can be of both vegetable or animal origin. Conventional stating materials are, for example, keratin, collagen, elastin, soy protein, rice protein, milk protein, wheat protein, silk protein or almond protein. A mixed material is produced by hydrolysis with a mixed molecular weight of from about 100 to about 50,000. Usually the average molecular weight is in a range of from about 500 to about 1000. Preferably the cationic derivatized protein hydrolyzates contain one or two long $C_8$- to $C_{22}$-alkyl chains and two or one short $C_1$- to $C_4$-alkyl groups. Compounds with the long alkyl chains are preferred.

Cationic silicone compounds are especially preferred as the hair care ingredient (B). They are substituted with a cationic or cationizable group. Suitable cationic silicone compounds preferably have either at least one amino group or at least one ammonium group. Suitable silicone polymers with amino groups are known as amodimethicone and trimethylsilylamodimethicone under the INCl nomenclature system. This compound is a polydimethylsiloxane with aminoalkyl substituent groups. The aminoalkyl groups can be terminal or side groups. Suitable aminoalkyl groups are those of the general formula (VI):

$$R^8R^9R^{10}Si\text{—}(OSi\ R^{11}R^{12})_x\text{—}(OSiR^{13}Q)_y\text{—}OSiR^{14}R^{15}R^{16} \qquad (VI),$$

wherein $R^8$, $R^9$, $R^{14}$ and $R^{15}$, independently of each other, are equal or different and each represent $C_1$- to $C_{10}$-alkyl, phenyl, hydroxy, hydrogen, $C_1$- to $C_{10}$-alkoxy or acetoxy, preferably $C_1$- to $C_4$-alkyl, especially preferably methyl, or trimethylsilyl;

$R^{10}$ and $R^{16}$ are the same or different and, independently of each other, represent —$(CH_2)_a$—$NH_2$ with a=1 to 6, $C_1$- to $C_{10}$-alkyl, phenyl, hydroxy, hydrogen, $C_1$- to $C_{10}$-alkoxy or acetoxy, preferably $C_1$- to $C_4$-alkyl, especially preferably methyl;

$R^{11}$, $R^{12}$ and $R^{13}$ are the same or different and independently of each other each represent hydrogen, a $C_1$- to $C_{20}$-substituted hydrocarbon group with at least one O and/or N atom substituent and an $C_1$- to $C_{20}$-unsubstituted hydrocarbon group, preferably a $C_1$- to $C_{10}$-alkyl or phenyl group, especially preferably a $C_1$- to $C_4$-alkyl group, most preferably methyl;

Q represents -A-N $R^{17}R^{18}$, or -A-N$^+R^{17}R^{18}$ $R^{19}$, wherein A stands for a divalent $C_1$- to $C_{20}$-alkylene compound group, which can contain an O—, N— or OH substituent group, and $R^{17}$, $R^{18}$ and $R^{19}$, independently of each other, are equal or different and represent hydrogen, a $C_1$- to $C_{22}$-substituted hydrocarbon group, preferably a $C_1$- to $C_4$-alkyl or phenyl group, preferably Q stand for —($CH_2)_3$—$NH_2$, —$(CH_2)_3NHCH_2CH_2NH_2$, —$(CH_2)_3OCH_2$—$CHOHCH_2NH_2$ and —$(CH_2)_3N(CH_2OH)_2$, —$(CH_2)_3$—$NH_3^+$ and —$(CH_2)_3OCH_2CHOH$—$CH_2N^+(CH_3)_2R^{20}$, wherein $R^{20}$ is a $C_1$- to $C_{22}$-alkyl residue; X represents a number between 1 and 10,000, preferably between 1 and 1000; and Y represents a number between 1 and 500, preferably between 1 and 50. The molecular weight of the amino-silicones is between 500 and 100,000 g/mol. The amine content (meq/g) is preferably in a range of from 0.05 to 2.3, especially preferably from 0.1 to 0.5.

Suitable silicone polymers with two terminal quaternary ammonium groups are known under the INCI name Quaternium-80. The silicone polymers are dimethylsiloxanes with two terminal aminoalkyl groups. The quaternary aminosilicones that are suitable have the following general formula (VII):

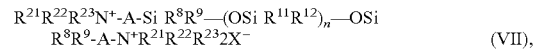

wherein A has the same significance as in the above formula (VI) and is preferably —$(CH_2)_3OCH_2CHOH$—$CH_2N^+(CH_3)_2R^{20}$, wherein $R^{20}$ is a $C_1$- to $C_{22}$-alkyl residue, which can have an OH group substitutent;

wherein $R^8$, $R^9$, $R^{11}$ and $R^{12}$ have the same significance as above in formula (IV) and are preferably methyl groups;

wherein $R^{21}$, $R^{22}$ and $R^{23}$, independently of each other, each represent a $C_1$- to $C_{22}$-alkyl residue, which can also contain hydroxy group substituents and wherein preferably at least one of the groups has at least 10 carbon atoms and the remaining groups have one to four carbon atoms; and n is a number from 0 to 200, preferably 10 to 100. These diquaternary polydimethylsiloxanes are marketed under the trademark ABIL® QUAT 3270, 3272 and 3274 of Goldschmidt, Germany.

The pearlescent or turbidity-inducing ingredient or agent (C) is selected from the group consisting of fatty acid alkanol amides, fatty acid glyceryl esters, guanine, glycol fatty acid diesters, styrene/acrylate copolymers, polyethylene glycol fatty acid diesters, styrene/vinylpyrrolidone copolymers and poly(trimethylammoniumethylmethacrylate chloride). Suitable fatty acid alkanol amides are those of the general formula VIII:

wherein $R^{24}$ represents a saturated or monounsaturated or polyunsaturated $C_7$- to $C_{21}$-hydrocarbon group, $R^{25}$ represents a $C_1$- to $C_4$-hydroxyalkyl group, which has at least one OH group and $R^{26}$ represents hydrogen or a $C_1$- to $C_4$-hydroxyalkyl group, which has at least one OH group. Preferably $R^{25}$ represents —$CH_2CH_2OH$, $R^{26}$ represents hydrogen or —$CH_2CH_2OH$ and $R^{24}$—$C(=O)$— represents a fatty acid group. Coconut fatty acid monoamide and coconut fatty acid diethanolamide (INCI name: cocamide MEA, cocamide DEA) are particularly preferred. Suitable fatty acid glyceryl esters are those of the general formula R'—C(=O)—O CH$_2$CH(OH)CH$_2$OH, wherein R' represents a saturated or monounsaturated or polyunsaturated $C_7$- to $C_{21}$-hydrocarbon group. Preferably R'—C(=O)— represents a fatty acid residue, especially preferably glyceryl monolaurate. Suitable glycol difatty acid esters are those of the general formula R"C(=O)O—$(CH_2CH_2O)_n$—C(=O)R", wherein n=1 and R" stands for a saturated or monounsaturated or polyunsaturated $C_7$- to $C_{21}$-hydrocarbon group. Preferably R"C(=O) stands for a fatty acid group, especially preferably ethylene glycol distearate. Suitable polyethylene glycol fatty acid diesters are those of the above-stated general formula, in which n is from 2 to 6. PEG-3 distearate is particularly preferred. Suitable styrene/acrylate copolymers are copolymers from styrene and at least one monomer. The monomers are selected from the group consisting of acrylic acid, methacrylic acid or their $C_1$- to $C_4$-alkyl esters, methacryl amides and acryl amides (INCI names: styrene/acrylates copolymer, styrene/acrylamide copolymer). A suitable poly(trimethylammoniumethylmethacrylate chloride), which has the INCI name: Polyquaternium-37), is obtained commercially under the trademark Salcare® SC96 (Ciba, Allied Colloids).

An especially beautiful and particularly stable pearlescence effect is obtained with a mixture of at least one fatty acid alkanol amide and at least one glycol fatty acid diester, especially a mixture of coconut fatty acid monoethanolamide or coconut fatty acid diethanol amide and glycol distearate. The compositions according to the invention preferably contain from 0.1 to 10, particularly preferably from 1 to 5, percent by weight of this mixture. The weight ratio of the fatty acid alkanol amide to glycol fatty acid diester is from 0.8:1 to 3:1.

The compositions according to the invention are packaged in an aqueous medium. The water content usually amounts to from 70 to 98, especially preferably from 80 to 95, percent by weight. The usual co-solvents can also be contained in the compositions of the invention as auxiliary ingredients. These co-solvents include, e.g. the lower monovalent alcohols with 2 to 5 carbon atoms, such as ethanol and isopropanol, or polyvalent alcohols, especially those with 2 to 5 carbon atoms, such as glycerol, ethylene glycol, propylene glycol, butylene glycol or pentandiol. The alcohol content preferably amounts to from 0.1 to 10, especially preferably from 0.5 to 5, percent by weight.

In a preferred embodiment the compositions according to the invention additionally contain at least one nonionic surfactant. Suitable nonionic surfactants are, for example, the nonionic emulsifiers described in "International Cosmetic Ingredient Dictionary and Handbook", 7th Edition, Volume 2, in the section "Surfactants—Emulsifying Agents". Suitable nonionic surfactants include preferably ethoxylated fatty acids with 10 to 26 carbon atoms, ethoxylated monovalent or multivalent alcohol with from one to six carbon atoms, ethoxylated fatty alcohols with 10 to 26 carbon atoms, ethoxylated hydrogenated or nonhydrogenated castor oil, alkyl polyglucosides, glyceride alkoxylates, fatty acid glyceride polyalkylene glycol ethers or partial glyceride polyalkylene glycol ethers with less than 30 alkylene glycol units respectively, for example polyethylene glycol-(7)-glyceryl cocoate, polyglycol amides, fatty acid sugar esters, ethoxylated fatty acid sugar esters and partial glycerides. The ethoxylation degree of these ethoxylated surfactants usually amounts to from 1 to 400, preferably 2 to 200, especially preferably 3 to 25. Fatty alcohol ethoxylates are particularly preferred as the nonionic surfactants. For example, alcohols with from 10 to 18, preferably 10 to 16, carbon atoms and an ethoxylation degree of preferably 2 to 200, especially preferably 3 to 25, are suitable. The compositions according to the invention containing the additional nonionic surfactants preferably contain from 0.01 to 5 percent by weight of these nonionic surfactants.

The compositions according to the invention furthermore also can contain additional cosmetic additive ingredients that are customary in hair treatment compositions. Examples of these cosmetic additive ingredients include, e.g., nonionic or anionic polymers, in so far as they are compatible with the remaining ingredients, in amounts of preferably from 0.01 to 10 percent by weight; perfume oils in an amount of preferably from 0.01 to 5 percent by weight; wetting agents or emulsifiers in an amount of preferably from 0.01 to 10 percent by weight; moisturizing agents, preservatives, bactericides and fungicides, such as 2,4,4-trichloro-2-hydroxydiphenylether, parabene or methylchloroisothiazolinone, in an amount of 0.01 to 1.0 percent by weight; buffer substances, such as sodium citrate or sodium phosphate, in an amount of 0.1 to 1.0 percent by weight; dye stuffs, e.g. fluorescein, sodium salt, in an amount of about 0.1 to 1.0 percent by weight; care materials, such as plant and vegetable extracts, protein and silk hydrolyzates, lanolin derivatives, in an amount of 0.1 to 5 percent by weight; light protective agents, antioxidants, radical trapping agents, antiflaking agents, luster-imparting substances, vitamins and de-fatting agents, in an amount of from 0.01 to 10 percent by weight.

The compositions according to the invention can have a pH in a pH-range of 2.0 to 9.5. Weakly acid pH values between 4.5 and 7, especially up to 6.5, are particularly preferred. Since preferred embodiments of the compositions according to the invention are acidic, they can contain organic or inorganic acids, such as formic acid, tartaric acid, malic acid, maleic acid, fumaric acid, glyoxylic acid, pyrrolidone carboxylic acid, citric acid, lactic acid, sulfuric acid, acetic acid, hydrochloric acid, phosphoric acid, among others.

The composition according to the invention preferably is in the form of a viscose cream or a fluid emulsion. The viscosity is preferably in a range of 300 to 6000 mPa·s, preferably from 500 to 4000 mPa·s, measured as a shear viscosity with a HAAKE VT-550 Rheometer, measuring body SV-DIN, at a temperature of 25° C. and a shear rate of 50 $s^{-1}$. This composition is filled, according to its consistency, into a suitable container or package, e.g. a tube, a cream pan or dish, a glass or plastic flask, a pump dispenser or an aerosol can together with a propellant gas. The packaging material is preferably transparent, or at least translucent. The packaging material for example, can be glass or transparent plastic, such as polyethylene, polypropylene or polyethylene terephthalate.

To make the compositions according to the invention the pearlescence or turbidity-inducing agent, in so far as it is a solid, is first melted. Then the resulting melted pearlescence or turbidity-inducing agent is emulsified in an aqueous solution of the remaining ingredients, with the exception of the thickener, at elevated temperatures, for example from 50 to 90° C., preferably 60 to 85° C. The cooled mass is then added to an aqueous solution of the associative thickener. Fluid pearlescence concentrate may be directly stirred into the cooled mass.

The method of use of the composition according to the invention comprises taking an amount of the composition from a package or container, which is sufficient to provide the conditioning action and distributing it on moist hair after washing the hair or on dry hair. The amount used depends on the abundance of the hair and usually is from 1 to 25 g. When preferably in use as a rinse product it is rinsed from the hair after a sufficient acting time, for example 1 to 15 minutes. Subsequently the hair is combed through as needed or put in a hairstyle and dried. When used as a leave-in product the composition of the invention is not rinsed from the hair after application.

The composition is characterized by reproducible quality in manufacture, because the product consistency and pearlescence are only a little effected by varying cooling conditions. The product is also characterized by a high stability. After three months in storage at 40° C. there are no changes in pearlescence and viscosity.

The following examples illustrate the subject matter of the invention more clearly, without limiting the appended claimed subject matter.

EXAMPLES

Example 1: Pearlescent Hair Care Composition

| | |
|---|---|
| 3.0 g | Coconut fatty acid monoethanol amide |
| 2.0 g | Abil ® Quat 3272 (Quaternium-80, 50% in propylene glycol) |
| 1.8 g | Propylene glycol |
| 1.2 g | Polyether-1 (Pure Thix ® TX-1442) |
| 0.75 g | Cetyl trimethyl ammonium chloride |
| 0.7 g | Tegobetain ® (30% in water, cocamidopropyl betaine) |
| 0.5 g | Laureth-4 |
| to 100 g | water |

Example 2: Pearlescent Hair Care Composition

| | |
|---|---|
| 3.33 g | Euperlan ® PK 4000 (40% gycoldistearate, 7.5% Laureth-4, 7.5% cocamidopropylbetaine in water) |
| 2.0 g | Coconut fatty acid monoethanol amide |
| 2.0 g | Abil ® Quat 3272 (Quaternium-80, 50% in propylene glycol) |
| 1.8 g | Propylene glycol |
| 1.2 g | Polyether-1 (Pure Thix ® TX-1442) |
| 0.75 g | Cetyl trimethyl ammonium chloride |
| 0.7 g | Tegobetain ® (30% in water, cocamidopropyl betaine) |
| 0.5 g | Laureth-4 |
| to 100 g | water |

Viscosity: about 2000 mPa·s, measured as shear viscosity with a HAAKE VT-550 Rheometer, Measurement body SV-DIN at a temperature of 25° C. and a shear rate of 50 s$^{-1}$. The hair care composition has a uniform viscosity and a stable pearlescence effect at 40° C. during a storage period of three months.

The term "aqueous cosmetic base" means that part of the composition of the invention comprising the solvent including the water and the cosmetic additive ingredients described above.

The disclosure in German Patent Application 101 47 501.2 of Sep. 26, 2001 is incorporated here by reference. This German Patent Application describes the invention described hereinabove and claimed in the claims appended hereinbelow and provides the basis for a claim of priority for the instant invention under 35 U.S.C. 119.

While the invention has been illustrated and described as embodied in pearlescent hair care compositions, it is not intended to be limited to the details shown, since various modifications and changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A pearlescent hair care composition consisting of an aqueous cosmetic base and a combination of
    at least one nonionic, amphiphilic associative thickener consisting of at least one hydrophobically modified aminoplast/polyether copolymer;
    at least one hair care active ingredient selected from the group consisting of cationic surfactants, zwitterionic surfactants, cationic polymers, cationic silicone compounds, amine-substituted silicone compounds, cationic derivatized proteins, cationic derivatized protein hydrolyzates, and betaines;
    at least one pearlescence or turbidity-inducing agent selected from the group consisting of fatty acid alkanol amides, fatty acid glyceryl esters, guanine, glycol fatty acid diesters, styrene/acrylate copolymers, polyethylene glycol fatty acid diesters, styrene/vinyl pyrrolidone copolymers and poly(trimethylammonium ethylmethacrylate chloride);
    in the aqueous cosmetic base;
    wherein said aqueous cosmetic base consists of water and at least one cosmetic ingredient selected from the group consisting of monovalent alcohols with 2 to 5 carbon atoms, polyvalent alcohols with 2 to 5 carbon atoms, nonionic surfactants, nonionic polymers, anionic polymers, perfume oils, moisturizing agents, preservatives, bactericides, fungicides, buffer substances, dyestuffs, plant extracts, vegetable extracts, protein hydrolyzates, silk hydrolyzates, light-protective agents, antioxidants, radical trapping agents, anti-flaking agents, luster-imparting substances, vitamins, organic acids for pH adjustment, inorganic acids for pH adjustment, and de-fatting agents; and
    wherein the nonionic polymers and/or the anionic polymers are contained in an amount of 0.01 to 10 percent by weight when present in the hair care composition; the perfume oils are contained in an amount of 0.01 to 5 percent by weight when present in the hair care composition; the preservatives, bactericides, and/or fungicides are contained in an amount of 0.01 to 1.0 percent by weight when present in the hair care composition; the buffer substances are contained in an amount of 0.1 to 1.0 percent by weight when present in the hair care composition; the dyestuffs are contained in an mount of 0.1 to 1.0 percent by weight when present in the hair care composition; the plant extracts, vegetable extracts, protein hydrolyzates, and silk hydrolyzates are contained in an amount of from 0.1 to 5 percent by weight when present in the hair care composition; and the de-fatting agents are contained in an amount of 0.01 to 10 percent by weight when present in the hair care composition.

2. The composition as defined in claim 1, containing from 0.1 to 5 percent by weight of said at least one nonionic, amphiphilic associative thickener, from 0.01 to 10 percent by weight of said at least one hair care active ingredient and from 0.1 to 10 percent by weight of said at least one pearlescence or turbidity-inducing agent.

3. The composition as defined in claim 1, wherein said at least one nonionic, amphiphilic associative thickener is at least one polymer of formula (I):

wherein Amp represents an aminoplast monomer or an aminoplast oligomer group or an aminoplast polymer group; AO represents an alkylene oxide group, R represents hydrogen, a $C_1$- to $C_4$-alkyl group of a $C_1$- to $C_4$-acyl group, x and y are greater than 1 and n is a positive number.

4. The composition as defined in claim 1, wherein said at least one nonionic, amphiphilic associative thickener is a reaction product of an acid catalyzed reaction of a glycoluril derivative compound, a polyalkylene glycol and an alkoxylated hydrocarbon.

5. The composition as defined in claim 1, wherein said at least one nonionic, amphiphilic associative thickener is selected from the group consisting of polyether-1, PEG-180/octoxynol-40/TMMG copolymer and PEG-180/Laureth-5/TMMG copolymer.

6. The composition as defined in claim 1, wherein said at least one hair care active ingredient is at least one of
cationic surfactants represented by formula III:

wherein $R^1$ to $R^4$ each represent, independently of each other, an aliphatic group, an aromatic group, an alkoxy group, a polyoxyalkylene group, an alkylamido group, a hydroxyalkyl group, an aryl group or an alkaryl group, each having 1 to 22 carbon atoms, and $X^{(-)}$ represents a cosmetically compatible anion;
cationic organic polymers selected from the group consisting of methyl-vinylimidazolium chloride/vinyl pyrrolidone copolymer, quaternized vinyl pyrrolidone/dimethylaminoethylmethacrylate copolymer, cationic derivatized polysaccharides, neutralized chitosan and neutralized chitosan derivative compounds; and
cationic silicone polymers comprising dimethylpolysiloxanes with terminal alkylammonium groups.

7. The composition as defined in claim 1, wherein said at least one pearlescence or turbidity-inducing agent is a fatty acid monoalkanol amide or fatty acid dialkanol amide of formula VIII:

wherein $R^{24}$ represents a saturated monounsaturated or polyunsaturated $C_7$- to $C_{21}$-hydrocarbon group, $R^{25}$ represents a $C_1$- to $C_4$-hydroxyalkyl group, which has at least one OH group and $R^{26}$ represents hydrogen or a $C_1$- to $C_4$-hydroxyalklyl group, which has at least one OH group.

8. The composition as defined in claim 1, containing from 1 to 5 percent by weight of a combination of at least one fatty acid monoalkanol amide or fatty acid dialkanol amide and at least one glycol fatty acid diester as said at least one pearlescence or turbidity-inducing agent and wherein said at least one fatty acid monoalkanol amide or fatty acid dialkanol amide and said at least one glycol fatty acid diester are present in said combination in a weight ratio of 0.8:1 to 3:1.

9. The composition as defined in claim 1, having a viscosity of 300 to 6000 mPa·s at 25° C. and a shear rate of 50 s$^{-1}$.

10. A pearlescent hair care composition consisting of an aqueous cosmetic base and a combination of
from 0.1 to 5 percent by weight at least one nonionic, amphiphilic associative thickener selected from the group consisting of polyether-1, PEG-180/octoxynol-40/TMMG copolymer and PEG-180/Laureth-50/TMMG copolymer;
from 0.01 to 10 percent by weight of at least one hair care active ingredient selected from the group consisting of cationic surfactants and cationic silicone compounds; and from 0.1 to 10 percent by weight of at least one glycol fatty acid diester and either a fatty acid monoalkanol amide, fatty acid dialkanol amide or a mixture of said amides, as a pearlescence of turbidity-inducing agent; in the aqueous cosmetic base.

11. A hair care product consisting of a transparent or translucent package or container and a pearlescent hair care composition, wherein said pearlescent hair care composition is packaged in said package or contained in said container; and wherein said pearlescent hair care composition consists of a combination in an aqueous cosmetic base, and wherein said combination consists of from 0.1 to 5 percent by weight at least one nonionic, amphiphilic associative thickener selected from the group consisting of polyether-1, PEG-180/octoxynol-40/TMMG copolymer and PEG-180/Laureth-50/TMMG copolymer; from 0.01 to 10 percent by weight of at least one hair care active ingredient selected from the group consisting of cationic surfactants and cationic silicone compounds; and from 0.1 to 10 percent by weight of at least one glycol fatty acid diester and either a fatty acid monoalkanol amide, fatty acid dialkanol amide or a mixture of said amides, as a pearlescence or turbidity-inducing agent.

12. A hair care product consisting of a transparent or translucent package or container and a pearlescent hair care composition, wherein said pearlescent hair care composition is packaged in said package or contained in said container; and wherein said pearlescent hair care composition consists of a combination in an aqueous cosmetic base and wherein said combination consists of at least one nonionic, amphiphilic associative thickener consisting of at least one hydrophobically modified aminoplast/polyether copolymer; at least one hair care active ingredient selected from the group consisting of cationic surfactants, zwitterionic surfactants, cationic polymers, cationic silicone compounds, amine-substituted silicone compounds, cationic derivatized proteins, cationic derivatized protein hydrolyzates and betaines; and at least one pearlescence or turbidity-inducing agent selected from the group consisting of fatty acid alkanol amides, fatty acid glyceryl esters, guanine, glycol fatty acid diesters, styrene/acrylate copolymers, polyethylene glycol fatty acid diesters, styrene/vinyl pyrrolidone copolymers and poly(trimethylammonium ethylmethacrylate chloride).

13. The hair care product as defined in claim 12, wherein the pearlescent hair care composition contains from 0.1 to 5 percent by weight of said at least one nonionic, amphiphilic associative thickener, from 0.01 to 10 percent by weight of said at least one hair care active ingredient and from 0.1 to 10 percent by weight of said at least one pearlescence or turbidity-inducing agent.

14. The hair care product as defined in claim 12, wherein said at least one nonionic, amphiphilic associative thickener is at least one polymer of formula (I):

wherein Amp represents an aminoplast monomer or an aminoplast oligomer group or an aminoplast polymer group; AO represents an alkylene oxide group, R represents hydrogen, a $C_1$- to $C_4$-alkyl group of a $C_1$- to $C_4$-acyl group, x and y are greater than 1 and n is a positive number.

15. The hair care product as defined in claim 12, wherein said at least one nonionic, amphiphilic associative thickener is a reaction product of an acid catalyzed reaction of a glycoluril derivative compound, a polyalkylene glycol and an alkoxylated hydrocarbon.

16. The hair care product as defined in claim 12, wherein said at least one nonionic, amphiphilic associative thickener is selected from the group consisting of polyether-1, PEG-180/octoxynol-40/TMMG copolymer and PEG-180/Laureth-50/TMMG copolymer.

17. The hair care product as defined in claim 12, wherein said at least one hair care active ingredient is at least one of cationic surfactants represented by formula III:

$$N^{(+)}R^1R^2R^3R^4 \, X^{(-)} \quad\quad\quad (III)$$

wherein $R^1$ to $R^4$ each represent, independently of each other, an aliphatic group, an aromatic group, an alkoxy group, a polyoxyalkylene group, an alkylamido group, a hydroxyalkyl group, an aryl group or an alkaryl group, each having 1 to 22 carbon atoms, and $X^{(-)}$ represents a cosmetically compatible anion;
  cationic organic polymers selected from the group consisting of methyl-vinylimidazolium chloride/vinyl pyrrolidone copolymer, quaternized vinyl pyrrolidone/dimethylaminoethylmethacrylate copolymer, cationic derivatized polysaccharides, neutralized chitosan and neutralized chitosan derivative compounds; and
  cationic silicone polymers comprising dimethylpolysiloxanes with terminal alkylammonium groups.

18. The hair care product as defined in claim 12, wherein said at least one pearlescence or turbidity-inducing agent is a fatty acid monoalkanol amide or fatty acid dialkanol amide of formula VIII:

$$R^{24}\text{---}C(\!=\!O)\text{---}NR^{25}R^{26} \quad\quad\quad (VIII)$$

wherein $R^{24}$ represents a saturated monounsaturated or polyunsaturated $C_7$- to $C_{21}$-hydrocarbon group, $R^{25}$ represents a $C_1$- to $C_4$-hydroxyalkyl group, which has at least one OH group and $R^{26}$ represents hydrogen or a $C_1$- to $C_4$-hydroxyalklyl group, which has at least one OH group.

19. The hair care product as defined in claim 12, wherein said pearlescent hair care composition contains from 1 to 5 percent by weight of a combination of at least one fatty acid diester and either a fatty acid monoalkanol amide, fatty acid dialkanol amide or a mixture of said amides, as said at least one pearlescence or turbidity-inducing agent, and wherein said at least one fatty acid monoalkanol amide or fatty acid dialkanol amide and said at least one glycol fatty acid diester are present in said combination in a weight ratio of 0.8:1 to 3:1.

20. The hair care product as defined in claim 12, wherein said pearlescent hair care composition has a viscosity of 300 to 6000 mPa·s at 25° C. and a shear rate of 50 $s^{-1}$.

* * * * *